United States Patent [19]

Sandberg

[11] Patent Number: 4,870,086
[45] Date of Patent: Sep. 26, 1989

[54] OPTICALLY PURE COMPOUND AND A PROCESS FOR ITS PREPARATION

[75] Inventor: Rune V. Sandberg, Järna, Sweden

[73] Assignee: Astra Lakemedel Aktiebolag, Sodertalje, Sweden

[21] Appl. No.: 934,114

[22] Filed: Nov. 24, 1986

[30] Foreign Application Priority Data

Jan. 3, 1986 [SE] Sweden ............................. 8600017

[51] Int. Cl.$^4$ ........................................... A61K 31/445
[52] U.S. Cl. ...................................... 514/330; 546/225
[58] Field of Search ........................ 546/225; 514/330

[56] References Cited

U.S. PATENT DOCUMENTS

| | | | |
|---|---|---|---|
| 2,248,018 | 7/1941 | Eisleb | 546/225 |
| 2,799,679 | 7/1957 | Ekenstam et al. | 546/225 |
| 3,551,431 | 12/1970 | Kuhnis et al. | 546/225 |
| 3,879,382 | 4/1975 | Watase et al. | 540/540 |
| 4,110,331 | 8/1978 | Pettersson | 546/225 |
| 4,302,465 | 11/1981 | Ekenstam et al. | 514/330 |

FOREIGN PATENT DOCUMENTS

| | | |
|---|---|---|
| 1770408 | 10/1971 | Fed. Rep. of Germany . |
| 85/00599 | 2/1985 | PCT Int'l Appl. . |
| 775749 | 5/1957 | United Kingdom . |
| 775750 | 5/1957 | United Kingdom . |
| 800565 | 8/1958 | United Kingdom . |
| 824542 | 12/1959 | United Kingdom . |
| 869978 | 6/1961 | United Kingdom . |
| 949729 | 2/1964 | United Kingdom . |

OTHER PUBLICATIONS

Luduena, F. P., *Annual Review of Pharmacology*, "Duration of Local Anaesthesia", 9, 503-520 (1969).
Tullar, B. F., *J. Med. Chem.*, "Optical Isomers of Mepivacaine and Bupivacaine", 14, 891-892 (1971).
Friberger, P. et al., *Acta Pharm. Suecica*, "Some Physicochemical Properties of the Racemates and the Optically Active Isomers of Two Local Anaesthetic Compounds", 8, 361-364 (1971).
Aberg, G., *Acta Pharmacol et Toxicol.* "Toxicological and Local Anaesthetic Effects of Optically Active Isomers of Two Local Anaesthetic Compounds", 31, 273-286 (1972).
Af Ekenstam, B., et al., *Acta Chemica Scandinavica*, "Local Anaesthetics I. N-Alkyl Pyrrolidine and N-Alkyl Piperidine Carboxylic Acid Amides", 11, 1183-1190 (1957).
Aberg, G., et al., *Acta Pharmacol. et Toxicol*, "Studies on the Duration of Local Anaesthesia: Structure/Activity Relationships in a Series of Homologous Local Anaesthetics", 41, 432-443 (1977).
Aberg, G., *Linkoping University Medical Dissertations*, "Studies on Mepivacaine and its Optically Active isomers with Special Reference to Vasaoactive Properties". No. 5, 32 pp. (1972).

*Primary Examiner*—Richard L. Raymond
*Attorney, Agent, or Firm*—White & Case

[57] ABSTRACT

Optically pure S-(−)-1-propyl-2',6'-pipecoloxylidide hydrochloride monohydrate, with the structural formula

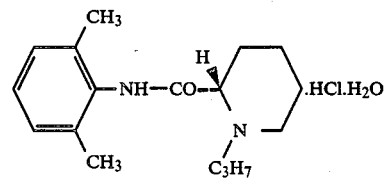

a process for the preparation thereof and the use for inducing local anesthesia.

6 Claims, No Drawings

OPTICALLY PURE COMPOUND AND A PROCESS FOR ITS PREPARATION

FIELD OF THE INVENTION

The present invention is directed to a new optically pure compound, a process for its preparation and its use in the manufacture of pharmaceutical preparations.

BACKGROUND OF THE INVENTION

A new local anesthetic namely (S)-(−)-1-propyl-2',6'-pipecoloxylidide hydrochloride is described in WO 85/00599. The new compound has an unexpected long duration compared to the racemate and the corresponding (R)-(+)-enantiomer. The preparation method described in WO 85/00599 gives however a product which contains about 10% of the (R)-(+)-enantiomer. This means that the product from a physical chemical point of view, contains only about 80% of the (S)-(−)-enantiomer, while the residual about 20% constitutes the racemic form. In addition the product obtained is hygroscopic and thus not stable and contains about 2% of water. One mole of water of crystallization implies a water content of 5,5%. A product having a varying content of water has the drawback that the percentage of water must be analyzed each time a pharmaceutical formulation shall be prepared. As the (S)-(−)-enantiomer is the most potent enantiomer a product containing less (R)-(+)-enantiomer was wanted. One object of this invention is thus to produce the compound in a form, which is stable and which does not change by storing at ordinary room temperature and humidity. A second object of this invention is to obtain a product consisting of the substantially pure (S)-(−)-ennantiomer.

OUTLINE OF THE INVENTION

The present invention is related to the monohydrate of (S)-(−)-1-propyl-2',6'-pipecoloxylidide hydrochloride. By means of a specific method of preparing the named hydrate, the (S)-(−)-enantiomer is obtained in high optical purity, namely ≧99.5%, even from an optically highly contaminated preparation. This specific method is a further aspect of this invention. The monohydrate of (S)-(−)-1-propyl-2',6'-pipecoloxylidide hydrochloride has the further advantage that it is very stable and hardly affected by drying in a desiccator over calcium chloride at room temperature and 0.5 mm Hg. Only when the compound was heated at 75° C. for 16 hours, other conditions being equal, the water of crystallization was removed. No further change of the compound was noticed.

PREPARATION

The monohydrate of (S)-(−)-1-propyl-2',6'-pipecoloxylidide hydrochloride with the structural formula

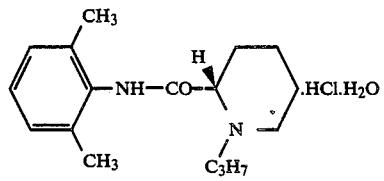

is prepared according to the invention by dissolving (S)-(−)-1-propyl-2',6'-pipecoloxylidide hydrochloride in water, whereupon hot acetone is added. The solution is then filtered as hot as possible and left for crystallization. At the preparation the starting compound is dissolved in an amount of water, which corresponds to about 1–3 times of the weight of the added compound and the volume of acetone added is 5–15 times of the water volume. If more water is added, that is an amount of water, which corresponds to up to 4 times of the weight of the added compound, the volume of the acetone added is 15–20 times of the water volume. It is especially preferred to make the preparation in the following way: The starting compound is heated with an amount of water equal to the weight of the starting compound. Hot acetone in such an amount that the compound is completely dissolved is added. Additional acetone to a volume of ten times of the volume of the added water is then poured into the solution, whereafter the solution is filtered and left for crystallization. The proportion between water and acetone is important. If too much acetone is added the product obtained is less pure and more recrystallizations are needed. When acetone less than 10 times the volume of water is added on the other hand the yield diminishes. The acetone added is hot preferably boiling (b.p. 56° C.). Acetone having a temperature between 45°–56° C. can be used according to the invention.

The invention also relates to pharmaceutical preparations containing the new pure compound as active ingredient: to the use of the new compound in therapy, especially for obtaining local anesthesia in mammals including man; to a method for obtaining local anesthesia in mammals including man by administering the new compound; and to the use of the new compound in the manufacture of pharmaceutical preparations having local anesthetic effect.

For the preparation of pharmaceutical preparations the new compound is dissolved in a liquid diluent, which is suitable for injection. The preparations used are aqueous solutions which contain between 1.25 and 15.0 mg/ml of the active compound calculated as the hydrochloride salt. In some applications a vasoconstrictor, epinephrine, is included in concentrations between 2.0 and 20.0 μg/ml calculated as the base. The solutions are made isoosmotic with physiologic saline by the addition of an appropriate amount of sodium chloride. Solutions containing epinephrine will also contain sodium metabisulphite in order to protect epinephrine from oxidation. pH of solutions without epinephrine is adjusted to approximately 5.5 wheras pH in solutions containing epinephrine is adjusted to approximately 3.6.

The invention is illustrated by the following examples.

Example 1 illustrates a specially preferred way of carrying out the process according to the invention.

EXAMPLE 1

Preparation of the monohydrate of (S)-(−)-1-propyl-2',6'-pipecoloxylidide hydrochloride. 82 g of the hydrochloride of (S)-(−)-1-propyl-2',6'-pipecoloxylidide containing 10% of the (R)-(+)-enantiomer was dissolved in 85 ml of water, whereupon acetone heated to its boiling point was added to a final volume of 850 ml. The solution was filtered and left for crystallization. This first recrystallization yielded 71,7 g. Another recrystallization was carried out by dissolving the obtained product in 72 ml of H₂O, whereupon boiling acetone to a final volume of 750 ml was added. The solution was filtered and left for crystallization. The final yield was 62.3 g (76%) of an optically pure (≧99.5%) product containing 5.4–5.6% of water, being the monohydrate of (S)-(−)-1-propyl-2',6'-pipecoloxylidide hydrochloride, melting interval 266°–267.5° C.

EXAMPLE 2

| | |
|---|---|
| (S)-(−)-1-propyl-2', 6'-pipecoloxylidide hydrochloride monohydrate | 2.64 mg |
| Sodium chloride | 8.53 mg |
| Sodium hydroxide to pH | 5.5 |
| Water for injection to | 1.0 ml |

2.64 mg of the monohydrate of (S)-(−)-1-propyl-2',6'-pipecoloxylidide hydrochloride was dissolved in 1 ml of sterile water. 8.53 mg of sodium chloride was added and the solution was adjusted to pH 5.5 with sodium hydroxide.

EXAMPLE 3

| | |
|---|---|
| (S)-(−)-1-propyl-2', 6'-pipecoloxylidide hydrochloride monohydrate | 5.29 mg |
| Epinephrine hydrogentartrate | 10.0 μg |
| Sodium chloride | 7.89 mg |
| Hydrochloric acid to pH | 3.6 |
| Water for injection to | 1.0 ml |

The preparation was prepared as described in Example 2

FURTHER ATTEMPTS TO PURIFY THE COMPOUND

In order to try to purify the product described in WO 85/00599 further recrystallizations from 2-propanol, the solvent used according to that patent application, were performed. Although water was added it was not possible to obtain an optically more pure or, with respect to the water contents, more well defined product.

Other common solvents such as methanol and ethanol are not suitable because of the too high solubility of the hydrochloride of (S)-(−)-1-propyl-2',6'-pipecoloxylidide in methanol and ethanol. In solvents such as ethyl acetate and dioxan on the other hand the compound is almost insoluble.

I claim:

1. (S)-(−)-1-propyl-2',6'-pipecoloxylidide hydrochloride, wherein the compound is in the form of its monohydrate.

2. The compound according to claim 1, wherein it is substantially optically pure.

3. The compound according to claim 1, wherein it contains less than 0.5% by weight of the corresponding (R)-(+)-enantiomer.

4. A process for the preparation of substantially optically pure monohydrate of (S)-(−)-1-propyl-2',6'-pipecoloxylidide hydrochloride, which comprises:
dissolving (S)-(−)-1-propyl-2',6'-pipecoloxylidide hydrochloride in a volume of water which is 1 to 3 times its weight;
adding acetone to the dissolved mixture in an amount which is 5 to 15 times the volume of the water added, wherein the temperature of the acetone is between 45° C. and its boiling point; and
isolating the monohydrate of (S)-(−)-1-propyl-2',6'-pipecoloxylidide hydrochloride.

5. The process according to claim 4, wherein the weight of the volume of water is equal to the weight of the (S)-(−)-1-propyl-2',6'-pipecoloxylidide hydrochloride and the volume of the acetone is 10 times the volume of the added water.

6. A method for inducing local anesthesia, which comprises adminstering to mammals including man needing local anesthesia an anesthetizing amount of the compound according to claim 1.

* * * * *

UNITED STATES PATENT AND TRADEMARK OFFICE

CERTIFICATE EXTENDING PATENT TERM
UNDER 35 U.S.C. § 156

PATENT NO.      :   4,870,086

ISSUED          :   September 26, 1989

INVENTOR(S)     :   Rune V. Sandberg

PATENT OWNER    :   Astra Läkemedel Aktiebolag

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,400 days from November 24, 2006, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 27th day of August 1998.

Bruce A. Lehman
Assistant Secretary of Commerce and
   Commissioner of Patents and Trademarks